United States Patent [19]

Kao et al.

[11] Patent Number: 5,670,664

[45] Date of Patent: Sep. 23, 1997

[54] PHOTOSENSITIVE ORGANIC COMPOUNDS THAT RELEASE CARBON MONOXIDE UPON ILLUMINATION

[75] Inventors: Joseph P. Y. Kao, Silver Spring; Paul F. Keitz, Baltimore, both of Md.

[73] Assignee: University Of Maryland Biotechnology Institute, Baltimore, Md.

[21] Appl. No.: 525,173

[22] Filed: Sep. 8, 1995

[51] Int. Cl.$^6$ .................................................. C07D 317/72
[52] U.S. Cl. ............... 549/336; 204/157.44; 204/157.47
[58] Field of Search ................................. 549/333, 336; 204/157.44, 157.47

[56] References Cited

PUBLICATIONS

Kao et al, "Caged Carbon Monoxide: Photolabile Molecules That Release Free Carbon Monoxide Upon Illumination", Abstract No. 2269, *The FASEB Journal*, 9:A392 (1995).

Birney et al, "Norborna–2,5–dien–7–one: A Covalent Benzene–Carbon Monoxide Adduct. A New Point on the Cycloreversion Structure–Reactivity Correlation Curve", *J. Am. Chem. Soc.*, 107:4553–4554 (1985).

Leblanc et al, "Observation and Substituent Control of Medium–Dependent Hot–Molecule Reactions in Low–Temperature Matrices", *J. Am. Chem. Soc.*, 110:7250–7252 (1988).

Kao et al, "Photosensitive Caged Compounds: Design, Properties, and Biological Applications", *Optical Microscopy: Emerging Methods and Applications*, pp. 27–85 (1993).

Kao, Poster, *Experimental Biology '95 Conference*, Atlanta, Georgia (Apr. 11, 1995).

Lev–Ram et al, *Neuron*, 15:407–415 (1995).

*Primary Examiner*—Nicky Chan
*Attorney, Agent, or Firm*—Sughrue, Mion, Zinn, Macpeak, and Seas

[57] ABSTRACT

The present invention relates to acetal derivatives of bicyclo [2.2.1]hepta-2,5-diene-7-one (norbornadienone) which are capable of releasing carbon monoxide upon irradiation with ultraviolet light, and a method for producing carbon monoxide employing the same.

16 Claims, 4 Drawing Sheets

PHOTOSENSITIVE ORGANIC COMPOUNDS THAT RELEASE CARBON MONOXIDE UPON ILLUMINATION

FIELD OF THE INVENTION

The present invention relates to acetal derivatives of bicyclo[2.2.1]hepta-2,5-diene-7-one (norbornadienone) which are capable of releasing carbon monoxide upon irradiation with ultraviolet (UV) light, and a method for producing carbon monoxide employing the same.

BACKGROUND OF THE INVENTION

Carbon monoxide (CO) is generated in living bodies by the action of heme oxygenases 1 and 2 (HO-1 and HO-2). Unlike HO-1, which is the heme-inducible enzyme in the liver and spleen that is responsible for degradation of heme from red blood cells, HO-2 is non-inducible, and is widely distributed in various tissues (Cruse et al, *J. Biol. Chem.*, 263:3348 (1988)). For example, HO-2 is found in high concentrations in the brain (Sun et al, *J. Biol. Chem.*, 265:8212 (1990)), an organ not functionally linked to the destruction of red blood cells. This strongly suggests a non-catabolic role for HO-2.

Guanylate cyclase is co-localized with HO-2 in the brain (Verma et al, *Science*, 259:381 (1993)). CO can activate guanylate cyclase (Marks et al, *Trends Pharmacol. Sci.*, 12:185 (1991)). This explains the ability of CO to inhibit platelet aggregation, and to cause smooth muscle relaxation (Marks et al, supra).

Also, CO is believed to mediate odorant responses in olfactory neurons (Verma et al, supra), and to serve as retrograde messenger for long term potentiation (LTP) in the hippocampus (Stevens et al, *Nature*, 364:147 (1993); and Zhuo et al, *Science*, 260:1946 (1993)).

In light of the foregoing, the role of CO in transmitting or transducing biological information has become an active area of research. As a result, CO has been used as a reagent in deciphering its role in biological signal transduction.

At present, the only known practical way of using CO as a reagent, especially in a living biological specimen, is to use CO gas. CO gas is generally dissolved in an aqueous solution, and then the solution is applied to the specimen. However, CO is extremely poisonous, as well as colorless and odorless. Thus, CO is very hazardous to handle. Furthermore, direct application of dissolved CO in an aqueous solution implies that an entire specimen is exposed chronically to CO. Such global and chronic exposure can have unpredictable effects. Moreover, the CO aqueous solution cannot be administered to the sample with temporal precision. Thus, there has been a desire in the art to develop techniques to release CO, a small molecule of gas, from a more complex, non-hazardous, precursor so as to avoid these difficulties.

Norbornadienone spontaneously decomposes to yield the highly stable molecule, benzene, and CO is concomitantly released:

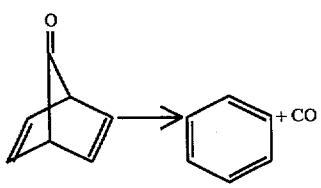

This decomposition reaction is so energetically favorable that it proceeds rapidly to completion at −60° C. This is not surprising because norbornadienone is a very highly strained, and thus an unstable molecule. Hence, norbornadienone cannot be used as a precursor under physiological conditions to deliver CO to a biological specimen.

A "caged" compound refers to an inert precursor molecule that can be transformed into a bioactive molecule by irradiation with light (Kao et al, In: "Optical Microscopy: Emerging Methods and Applications", Herman et al, Eds., Academic Press (1993)). Caging has been found to be an effective way of delivering a variety of biologically active molecules, such as cyclic nucleotides (Nerbonne et al *Nature* (London), 310:74 (1984), D-myo-inositol-1,4,5-trisphosphate (Walker et al, *Biochem.*, 28:3272 (1989); and calcium ions (Adams et al, *J. Am. Chem. Soc.*, 110:3212 (1988); and Ellis-Davies et al, *Proc. Natl. Acad. Sci., USA*, 91:187 (1994)). Caging is especially useful when the molecule is difficult to administer directly due to inconvenient physical or chemical properties of the molecule, e.g., nitric oxide, such as instability or reactivity (Makings et al, *J. Biol. Chem.*, 269:6282 (1994)).

Photosensitive norbornadienone derivatives, i.e., caged compounds, have been prepared for research purposes in physical chemistry (Birney et al, *J. Am. Chem. Soc.*, 107:4553 (1985); and LeBlanc et al, *J. Am. Chem. Soc.*, 110:7250 (1988)). Upon illumination with UV light, these derivatives generate norbornadienone, which subsequently decomposes to CO. However, these norbornadienone derivatives are disadvantageous because they absorb UV light very poorly, thus making rapid photoconversion to CO difficult in practical applications. Also, conversion of these derivatives by UV light appears to work best at very low temperatures (−258° C. and −263° C.), and in non-polar, non-aqueous media. Further, with these compounds, progressively more non-productive side-reactions occur as the temperature is raised, making use of such at physiological temperatures unfeasible. Thus, the known norbornadienone derivatives are not useful in biological applications.

The present invention overcomes the existing hazards and difficulties of using CO gas, as well as the difficulties of using known norbornadienone derivatives. The compounds of the present invention make it possible to deliver, with temporal precision, controlled, small, non-hazardous doses of CO to spatially restricted sites in living biological samples.

SUMMARY OF THE INVENTION

An object of the present invention is to provide reagents capable of generating CO upon illumination with UV light.

Another object of the present invention is to provide biologically inert compounds which can be taken up by cells, and will remain stable inside of cells until irradiated, at which time CO will be generated inside of the cells.

Still another object of the present invention is to provide a method for rapidly delivering controlled, small, non-hazardous doses of CO to spatially restricted sites in living biological samples at physiological temperatures.

These and other objects of the present invention, which will be apparent from the detailed description of the invention provided hereinafter, have been met in one embodiment by a compound represented by Formula (I):

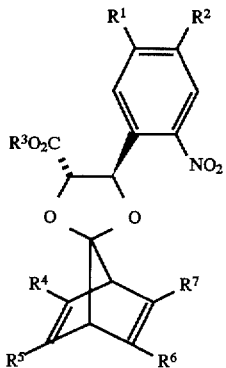

wherein $R^1$ and $R^2$, which may be the same or different, are each selected from the group consisting of hydrogen, hydroxy, alkanoyloxymethoxy, wherein the alkanoyloxy moiety has from 1 to 5 carbon atoms, preferably from 2 to 3 carbon atoms, alkyl having from 1 to 5 carbon atoms, preferably from 1 to 2 carbon atoms, and alkoxy having from 1 to 5 carbon atoms, preferably from 1 to 2 carbon atoms; with the proviso that $R^1$ and $R^2$ may be combined to form a methylenedioxy (O—$(CH_2)_n$—O) linkage, wherein n represents an integer of from 1 to 4, preferably from 1 to 2;

wherein $R^3$ is selected from the group consisting of hydrogen; alkyl having from 1 to 5 carbon atoms, preferably from 1 to 2 carbon atoms; alkanoyloxymethyl, wherein the alkanoyloxy moiety has from 1 to 5 carbon atoms, preferably from 2 to 3 carbon atoms; alkali metal ion, preferably lithium, sodium, potassium and cesium; alkaline earth metal ion, preferably calcium and magnesium; and $NR_4$, wherein each R, which may be the same or different, is selected from the group consisting of hydrogen, alkyl having from 1 to 5 carbon atoms, phenyl, tolyl and benzyl; and wherein $R^4$, $R^5$, $R^6$, $R^7$, which may be the same or different, are each selected from the group consisting of hydrogen, cyano, $CONHR^1$, $CONR^1_2$, $SO_2NR^1$, $SO_2NR^1_2$, $CH_2R^1$, $CH_2CONHR^1$, $CH_2CONR^1_2$, $CO_2R^3$ and $SO_3$, $R^3$, wherein $R^1$ and $R^3$ are as defined above.

In another embodiment, the above-described objects of the present invention have been met by a method for producing CO comprising the step of UV irradiating a compound represented by Formula (I).

DETAILED DESCRIPTION OF THE INVENTION

Figure 1:
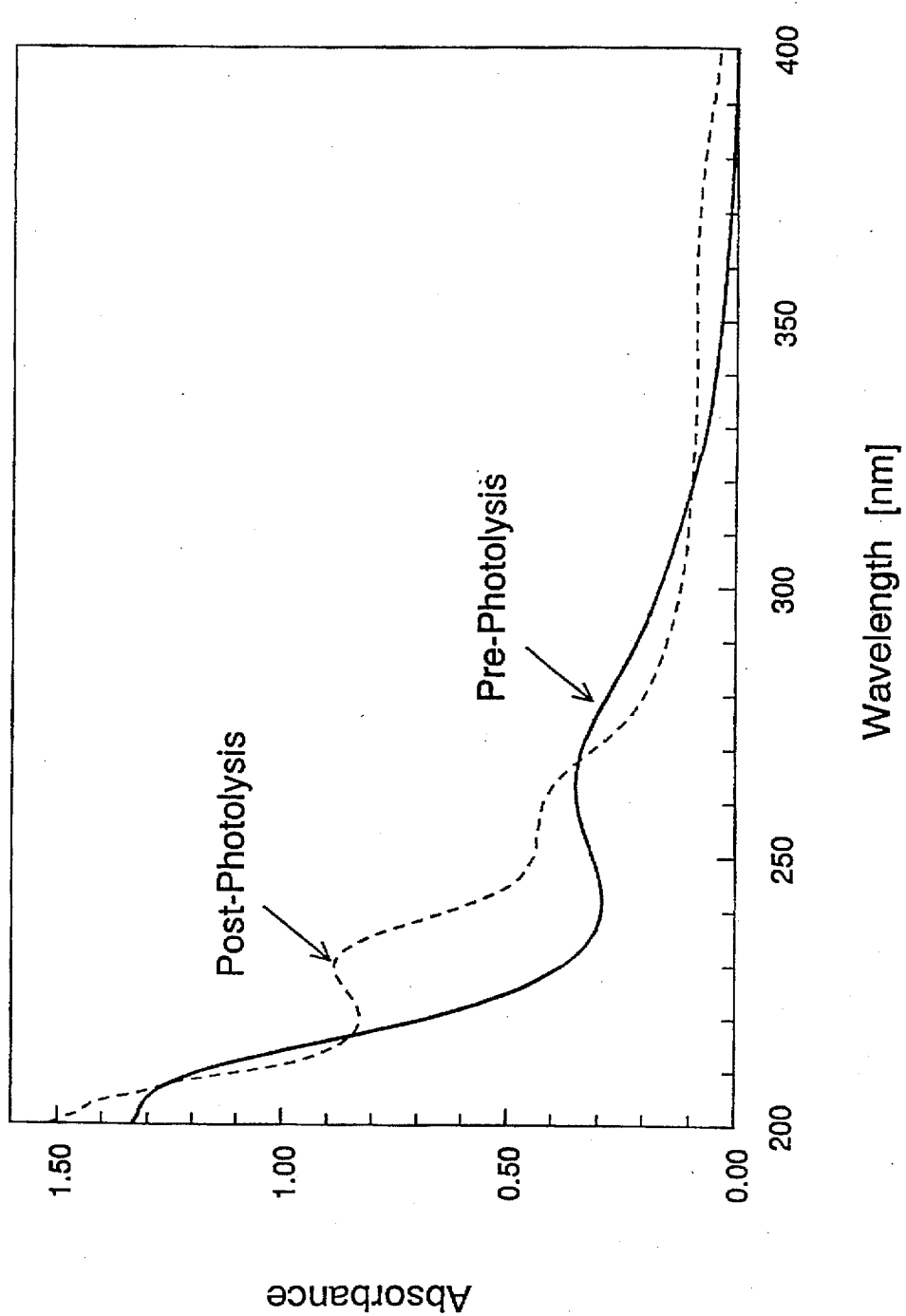
FIG. 1 shows the UV spectra of an aqueous solution of NF-CO/Na before and after photolysis with UV light.

As discussed above, in one embodiment, the above-described objects of the present invention have been met by a compound represented by Formula (I).

In the compounds of the present invention:

(1) the ketone carbonyl group in norbornadienone is chemically masked so that spontaneous decomposition is forestalled, and (2) the masking group is made photolabile so that photolysis can be used to cleave off the masking group and regenerate intact norbornadienone, which then rapidly and spontaneously decomposes to yield CO.

In a preferred embodiment, the masking group used is a 3-(2-nitrophenyl)-2,3-dihydroxypropionate, or a derivative thereof, wherein additional substituents on the phenyl ring increase the UV absorbance and/or shift the UV absorption bands to a longer wavelength (hereinafter an "auxochromic derivative"). Such masking groups are very sensitive to photolysis by near-UV light.

The compounds of the present invention are biologically inert, can be taken up by cells, and will remain stable until irradiated, at which time CO is released. Thus, a way of instantaneously generating intracellular CO is made available by the compounds of the present invention.

In addition, by using a microscope, light can be narrowly focussed on a sample, even at the single cell level, so that highly localized administration of CO can be achieved. Moreover, because light flashes can be very short and intense, CO can be generated at a precise instant with sub-second time resolution. In addition, varying doses of CO can be delivered by varying the intensity and/or duration of the light flashes, allowing dose-response relationships to be studied. The compounds of the present invention also exhibit little toxicity, and are easily loaded into cells.

In Formula (I), $R^1$ and $R^2$ are preferably each selected from the group consisting of hydrogen and methoxy, or when $R^1$ and $R^2$ are combined, they form —$OCH_2O$—.

$R^3$ preferably is selected from the group consisting of methyl, ethyl, acetoxymethyl, sodium and potassium. Sodium and potassium are the preferred ions employed in the present invention because these ions are the major monovalent cations present in normal intracellular and extracellular aqueous solutions, and thus are well-tolerated by living cells. More preferably, $R^3$ is an alkanoyloxymethyl, e.g., acetoxymethyl ($CH_2O_2CCH_3$) (AM) ester. These compounds can be directly loaded into living cells. This is because these esters mask the negative charge on the carboxyl group, and the resulting compounds are neutral and hydrophobic, such that they easily diffuse across biological membranes. Once inside the cells, however, the esters are readily hydrolyzed by non-specific esterases to yield the caged CO molecules, which are negatively charged, and unable to cross biological membranes, and thus become trapped and accumulate inside the cells.

In Formula (I), each R is preferably hydrogen.

In Formula (I), $R^4$, $R^5$, $R^6$, $R^7$ are preferably each hydrogen.

Specific examples of the compounds of the present invention include bicyclo[2.2.1]hepta-2,5-diene-7-one, cyclic 1-(2-nitrophenyl)-2-methoxycarbonyl-1,2-ethanediyl acetal (NF-CO/Me); bicyclo[2.2.1]hepta-2,5-diene-7-one, cyclic 1-(2-nitrophenyl)-2-carboxy-1,2-ethanediyl acetal, sodium salt (NF-CO/Na); bicyclo[2.2.1]hepta-2,5-diene-7-one, cyclic 1-(2-nitrophenyl)-2-acetoxymethyloxycarbonyl-1,2-ethanediyl acetal (NF-CO/AM); bicyclo[2.2.1]hepta-2,5-diene-7-one, cyclic 1-(4,5-dimethoxy-2-nitrophenyl)-2-ethoxycarbonyl-1,2-ethanediyl acetal (NV-CO/Et); bicyclo[2.2.1]hepta-2,5-diene-7-one, cyclic 1-(4,5-dimethoxy 2-nitrophenyl)-2-carboxy-1,2-ethanediyl acetal, sodium salt (NV-CO/Na); bicyclo[2.2.1]hepta-2,5-diene-7-one, cyclic 1-(4,5-dimethoxy-2-nitrophenyl)-2-acetoxymethyloxycarbonyl-1,2-ethanediyl acetal (NV-CO/AM); bicyclo[2.2.1]hepta-2,5-diene-7-one, cyclic 1-(4,5-methylenedioxy-2-nitrophenyl)-2-ethoxycarbonyl-1,2-ethanediyl acetal (NP-CO/Et); bicyclo[2.2.1]hepta-2,5-diene-7-one, cyclic 1-(4,5-methylenedioxy-2-nitrophenyl)-2-carboxy-1,2-ethanediyl acetal, sodium salt (NP-CO/Na); and bicyclo[2.2.1]hepta-2,5-diene-7-one, cyclic 1-(4,5-methylenedioxy-2-nitrophenyl)-2-acetoxymethyloxycarbonyl-1,2-ethanediyl acetal (NP-CO/AM).

UV light generally is considered to have a wavelength of 200 to 400 nm. In the present invention, any light within this wavelength range can be employed. However, from the standpoint of biological compatibility, it is preferred that the wavelength employed be in the range of 300 to 400 nm, as UV at wavelengths below 300 nm can damage proteins and nucleic acids in cells.

The temperature at which UV illumination is carried out is not critical to the present invention, and can be any temperature which does not adversely effect living cells. Generally, illumination is carried out at about 10° to 40° C.

The duration of UV illumination is not critical to the present invention, and will depend upon the intensity of the light source. Examples of such light sources include a mercury lamp and a xenon lamp.

The compounds of the present invention can be used in the method of present invention in the form of an aqueous solution. The concentration of the compounds of the present invention in the aqueous solution is not critical to the present invention. Generally, the concentration will be about $10^{-5}$ to $10^{-1}$ M.

The pH of the aqueous solution is not critical to the present invention, and generally is about 6 to 8.

The pH can be maintained using any suitable buffering system, such as a phosphate or HEPES (N-2-hydroxyethlypiperazine-N'-2-ethanesulfonate) buffer.

The compounds of the present invention can be used in an aqueous bath of culture media so as to perfuse tissues or cultured cells. UV illumination of the culture medium bathing the tissue or cells liberates free CO, which readily crosses biological membranes, and can thus enter the cells.

Alternatively, an aqueous solution of the compounds of the present invention can be introduced into living cells through either microinjection or patch pipets. The caged CO molecules, being negatively charged, are retained in the injected cells. Flashing the cells with UV light will generate CO from within loaded cells.

The compounds of the present invention can be prepared in general by acetal formation between silyl ethers of the caging group (3-(2-nitrophenyl)-2,3-dihydroxypropionate or auxochromic derivatives thereof) and tetracyclo[3.2.0.0$^{2,7}$.0$^{4,6}$]heptan-3-one (quadricyclanone), followed by palladium-catalyzed rearrangement of the resulting products.

The compounds of the present invention are useful, inter alia, for elucidating the role that CO plays in signal transduction in the nervous system, and in modulating neuronal plasticity in the nervous system (Dawson et al, *J. Neurosci.*, 14:5147 (1994); Izquierdo, *FASEB J.*, 8:1139 (1994); and Hawkins et al, *J. Neurobio.*, 25:652 (1994)).

The following examples are provided for illustrative purposes only and are in no way intended to limit the scope of the present invention.

In the following Synthesis Examples, the reagents and solvents used were ACS or HPLC grade, and used as received from the supplier, e.g., Aldrich, Fisher or VWR, unless otherwise stated. Tetrahydrofuran (THF) was distilled from potassium/benzophenone ketyl prior to use. Dichloromethane (DCM) was stored over 3 Å molecular sieves. Quadricyclanone was prepared as described by Gassman et al, *J. Am. Chem. Soc.*, 90:7276 (1968).

All reactions were performed under an inert argon atmosphere. All reaction glassware, syringes and needles were dried in an oven at 130° C. for at least 3 hr, then cooled under a stream of argon gas or in a desiccator prior to use.

The progress of most reactions was monitored by thin layer chromatography (tlc). Thin layer chromatography was performed on aluminum sheets coated with silica gel 60 F254 (E. Merck), and elution was performed with ethyl acetate in hexane or benzene.

The products were purified by column chromatography as described by Still et al, *J. Org. Chem.*, 43:2923 (1978), using silica gel 60 (230–400 mesh, E. Merck).

Melting points were recorded on a Mel-Temp II (Laboratory Devices) apparatus coupled to an Omega (Omega Engineering) HH23 digital thermometer. All of the melting points reported were uncorrected.

The structures of all of the purified products were established by NMR spectral analysis. Spectra were recorded on a General Electric QE-300 (300 MHz) NMR spectrometer. All samples were dissolved in CDCl$_3$ unless otherwise stated. Resonances reported below are in the following format: NMR (solvent): chemical shift in ppm downfield from tetramethylsilane, multiplicity (s=singlet, d=doublet, t=triplet, q=quartet, m=multiplet, b=broad), spin-spin coupling constant (if appropriate), integrated number of protons, and structural assignment. In certain instances, several adjacent peaks were too close for their integrals to be quantified individually, in which case, the integral for the entire group is reported.

SYNTHESIS EXAMPLE 1

Methyl 2,3-dihydroxy-3-(2-nitrophenyl)propionate (Compound IIa) was prepared by adding 250 mg of osmium tetroxide (0.984 mmol) in one portion to a 0° C. solution of 15 g of methyl trans-3-(2'-nitrophenyl)propenoate (72.4 mmol) (Compound Ia) and 12.7 g of N-methylmorpholine-N-oxide (0.108 mol) in a solution containing 25 ml each of H$_2$O, acetone and t-butanol (1:1:1). The reaction was warmed to room temperature, then stirred for 6 hr. Then, 50 ml of a freshly prepared solution of 20% (v/v) NaHSO$_3$ was added slowly over 30 min to destroy excess oxidant. Several scoops of NaCl were added to the resulting reaction mixture, and then the product was extracted 3 times, each with 200 ml of ether. The combined extracts were washed with 150 ml of a saturated NaCl solution (brine), dried over MgSO$_4$, and then concentrated in vacuo. The crude product, a light brown solid, was purified by recrystallization from ethanol to give 15.3 g (87% yield) of Compound IIa. M.p. 125.6–127.6° C.

$^1$H NMR (300 MHz, acetone-d$_6$), delta 3.75 (s, 3H, —OCH$_3$), 4.21 (d, J=8 Hz, 1H, MeO$_2$C—CH—OH), 4.48 (b, 1H, MeO$_2$C—CH—OH), 5.02 (d, J=6 Hz, 1H, Ar—C H—OH), 5.65 (b, 1H, Ar—CH—OH), 7.54 (t, J=8 Hz, Ar 5-H), 7.72 (t, J=8 Hz, Ar 4-H), 7.96 (d, J=8 Hz, Ar 3-H), 8.00 (d, J=8 Hz, Ar 6-H).

Methyl 2,3-bis(trimethylsilyloxy)-3-(2-nitrophenyl)propionate (Compound IIIa) was prepared by slowly adding 5.8 ml of chlorotrimethylsilane (45 mmol) dropwise to a stirring 0° C. mixture of 5.0 g of the diol, Compound IIa (20.7 mmol), and 8.7 ml of triethylamine (TEA, 62 mmol) in 30 ml of dry DCM (the diol was not soluble in DCM). After the addition was complete, the mixture was warmed to room temperature, and the silylation was complete 3 hr later.

40 ml of ethyl acetate was then added to the mixture, which was then cooled in an ice bath. The precipitated TEA-HCl was filtered off and rinsed with 20 ml of cold ethyl acetate. The filtrate was washed with 50 ml of water, 50 ml of brine, dried over $MgSO_4$, and concentrated to give an off-white solid. 100 ml of ethyl acetate was added to the product, and the undissolved solids were removed by filtration. The solvent was then removed to give 7.31 g of a cream-colored solid (91% yield) of Compound IIIa which did not need further purification. M.p. 57.1°–59.2° C.

$^1$H NMR delta −0.20 (s, 9H, $MeO_2C$—CH—OSi(C$H_3$)$_3$), −0.03 (s, 9H, Ar—CH—OSi(C$H_3$)$_3$), 3.78 (s, 3H, —OCH$_3$), 4.64 (d, J=2 Hz, 1H, $MeO_2C$—C$H$—OTMS), 5.74 (d, J=2 1H, Hz, Ar—C$H$—OTMS), 7.44 (t, J=8 Hz, 1H, Ar 5-H), 7.63 (t, J=7 Hz, 1H, Ar 4-H), 7.91 (dd, J=8, 1 Hz, Ar 3-H), 7.94 (dd, J=8, 1 Hz, Ar 6-H).

Tetracyclo[3.2.0.0$^{2,7}$.0$^{4,6}$]heptan-3-one, cyclic 1-(2-nitrophenyl)-2-methoxycarbonyl-1,2-ethanediyl acetal (Compound IVa) was prepared by adding 75 μl of trimethylsilyltriflate (0.39 mmol) to a −78° C. solution of 100 mg of quadricyclanone (0.94 mmol), and 363 mg of the disilylether, Compound IIIa (0.94 mmol) in 2.0 ml of dry DCM. After 5 min, the mixture was warmed to 0° C., and within a couple of min the amber solution became burgundy in color. When the burgundy color began to fade to an orange/red color, 3.0 ml of a saturated $NaHCO_3$ solution was added to quench the reaction. The mixture was stirred for about 1 min, then extracted 3 times, each with 5.0 ml of DCM. The organic extracts were washed with 5.0 ml of brine, dried over $Na_2SO_4$, and concentrated. The product was purified chromatographically using 2.5% (v/v) ethyl acetate in benzene to give 88 mg (28% yield) of Compound IVa, a light yellow oil.

$^1$H NMR delta 1.37 (dt, J=5, 1 Hz, 1H, bridgehead H), 1.68 (dt, J=5, 1 Hz, 1H, bridgehead H), 1.90 (m, 4H, quadricylane H's), 3.84 (s, 3H, —OCH$_3$), 4.53 (d, J=6 Hz, $MeCO_2$—C$H$—OR), 6.04 (d, J=6 Hz, Ar—C$H$—OR), 7.53 (t, J=8 Hz, Ar H-5), 7.73 (t, J=8 Hz, 1H, Ar H-4), 8.04 (d, J=7 Hz, 1H, Ar H-3), 8.07 (d, J=8 Hz, 1H, Ar H-6).

Next, a solution containing 550 mg of Compound IVa (1.67 mmol) and 2.0 mg, i.e., a catalytic amount, of dichloropalladium norbornadiene complex (7.0 μmol) in $CHCl_3$ was heated to 45° C. overnight. The solvent was removed, and the product was chromatographed using 20% (v/v) ethyl acetate in hexane to give 339 mg (62% yield) of bicyclo [2.2.1]hepta-2,5-diene-7-one, cyclic 1-(2-nitrophenyl)-2-methoxycarbonyl-1,2-ethanediyl acetal (NF-CO/Me) (Compound Va), which contained 5.0% of the starting material.

$^1$H NMR delta 3.70 (m, 1H, bridgehead H), 3.80 (s, 1H, —CO$_2$CH$_3$), 3.90 (m, 1H, bridgehead H), 4.33 (d, J=5 Hz, 1H, $MeO_2C$—C$H$—OR), 5.83 (d, J=5 Hz, 1H, Ar—C$H$—OR), 6.74–6.83 (m, 1H, vinyl H's), 7.50 (dt, J=8, 2 Hz, 1H, Ar H-5), 7.70 (dt, J=7, 1 Hz, 1H, Ar H-4), 6.75 (dd, J=8, 2 Hz, 1H, Ar H-3), 8.04 (dd, J=8, 1 Hz, 1H, Ar H-6).

Bicyclo[2.2.1]hepta-2,5-diene-7-one, cyclic 1-(2-nitrophenyl)-2-carboxy-1,2-ethanediyl acetal, sodium salt (NF-CO/Na) (Compound VIa) was prepared by adding 250 mg of a solution of Compound Va (0.759mmol) in 1.0 ml of methanol to a 1.0M sodium hydroxide solution (0.759 ml). The reaction was complete in 4 hr. The solvent was removed by rotary evaporation and any residual water present was removed by lyophilization. The yield was quantitative.

$^1$H NMR delta 3.85 (m, 2H, bridgehead H), 4.35 (d, J=5 Hz, 1H, —O$_2$C—C$H$—O—), 5.68 (d, J=5 Hz, 1H, Ar—C$H$—O—), 6.81–6.90 (m, 4H, vinyl H), 7.65 (t, J=8 Hz, 1H, Ar H-4), 7.71 (d, J=7 Hz, 1H, Ar H-3), 7.85 (t, J=8 Hz, Ar H-5), 8.04 (d, J=7 Hz, 1H, Ar H-6).

Bicyclo[2.2.1]hepta-2,5-diene-7-one, cyclic 1-(2-nitrophenyl)-2-acetoxymethyloxycarbonyl-1,2-ethanediyl acetal (NF-CO/AM) (Compound VIIa) was prepared by adding 164 mg of tetrabutylammonium iodide (0.45 mmol) to an undissolved mixture of 150 mg of Compound VIa (0.45 mmol) in dry DCM. When the solution cleared, it was cooled to 0° C., and 136 mg of bromomethylacetate (0.889 mmol, 87 μl) was added. After 1 hr, the reaction was warmed to room temperature, and stirred for another 2 hr. The solvent was removed and the product was purified by chromatography using 5.0% (v/v) ethyl acetate in benzene to give 114 mg (75% yield) of Compound VIIa, an amber oil.

$^1$H NMR delta 2.16 (s. 3H, —O(CO)—CH$_3$), 3.73 (b, 1H, bridgehead H), 3.98 (b, 1H, bridgehead H), 4.34 (d, J=6 Hz, 1H, $RO_2C$—C$H$—OR'), 5.80–5.86 (m, 3H, —CO$_2$—C$H_2$—OAc, Ar—C$H$—OR), 6.74–6.83 (m, 4H, vinyl H's), 7.50 (dt, J=8, 2 Hz, Ar H-5), 7.68–7.77 (m, 2H, Ar H-3, H-4), 8.05 (d, J=8, Ar 6-H).

SYNTHESIS EXAMPLE 2

Ethyl 3-(4,5-methylenedioxy-2-nitrophenyl)propenoate (Compound Ib) was synthesized by adding dropwise, 20 ml of a THF solution containing 6.89 g of triethyl phosphonoacetate (6.10 ml, 30.75 mmol) to a 0° C. mixture of 1.23 g of NaH (as a 60% (v/v) mineral oil suspension, 30.75 mmol) in 30 ml of dry THF, which action caused evolution of hydrogen gas. After the reaction mixture was stirred for 15 min, a solution containing 5.0 g (25.6 mmol) of 5-nitropiperonal in 30 ml of THF was added dropwise. The reaction was allowed to warm to room temperature, and after 2 hr was poured onto ice-cold about 1.5 M phosphate buffer (pH 5.0). The product was extracted 3 times, each with 75 ml of ether. The combined ether extracts were washed with 75 ml of brine, dried over MgSO$_4$, and the solvent was removed by rotary evaporation. The crude product was recrystallized from absolute ethanol to give 6.07 g (81% yield) of Compound Ib, an amber solid. M.p. 110.3°–111.6° C.

$^1$H NMR delta 1.34 (t, J=7, 2H, —O—CH$_2$—CH$_3$), 4.27 (q, J=7, 2H, —O—CH$_2$—CH$_3$), 6.16 (s, 2H, —O—CH$_2$—O—), 6.25 (d, J=16 Hz, —CH—C$H$—CO$_2$Et), 6.98 (s, 1H, piperonyl H-2), 7.54 (s, 1H, piperonyl H-5), 8.09 (d, J=16 Hz, 1H, Ar—C$H$—CH—).

The same dihydroxylation procedure used above for synthesizing Compound IIa was utilized for making ethyl 2,3-dihydroxy-3-(4,5-methylenedioxy-2-nitrophenyl) propionate (Compound IIb) using Compound Ib in place of Compound Ia. Compound IIb was recrystallized from an ethanol/water mixture. The synthetic yield of Compound IIb, and physical properties were as follows.

Large, yellow needles obtained in 85% yield. M.p. 165.4°–166.2° C.

$^1$H NMR (300 MHZ) delta 1.25 (t, J=7 Hz, 3H, —O—CH$_2$—CH$_3$), 4.11 (d, J=8 Hz, 1H, —CH—OH—CO$_2$Et), 4.21 (q, J=7 Hz, 2H, —OCH$_2$—CH$_3$), 4.42 (dd, J=8 and 2 Hz, —C$H$—OH—CO$_2$Et), 4.99 (d, J=6 Hz, 1H, Ar—CH—O$H$—), 5.69 (dd, J=6 and 2 Hz, 1H, Ar—C$H$—OH—), 6.22 (s, 2H, —O—C$H$—O—), 7.40 (s, 1H, piperonyl H—5), 7.49 (s, 1H, piperonyl H-2).

Ethyl 2,3-bis(trimethylsilyloxy)-3-(4,5-methylenedioxy-2-nitrophenyl)propionate (Compound IIIb) was synthesized from Compound IIb using the same procedure for preparing Compound IIIa from Compound IIa. Compound IIIb did not require purification. The physical and spectral data were as follows:

Yellow/brown needles obtained in 90% yield. M.p. 73.6°–79.1° C.

$^1$H NMR delta −0.13 (s, 9H, EtO$_2$C—CH—OSi(CH$_3$)$_3$), −0.01 (s, 9H, Ar—CH—OSi(CH$_3$)$_3$), 1.32 (t, J=7 Hz, 3H, —OCH$_2$CH$_3$), 4.23 (q, J=7 Hz, 2H, —OCH$_2$CH$_3$), 4.58 (d, J=2 Hz, 1H, EtO$_2$C—CH—OTMS), 5.81 (d, J=2 Hz, 1H, Ar—CHOTMS), 6.12 (s, 1H, —O—CH—O—), 7.36 (s, 1H, Ar 3-H), 7.46 (s, 1H, Ar 6-H).

Tetracyclo[3.2.0.0$^{2,7}$.0$^{4,6}$]heptan-3-one, cyclic 1-(4,5-methylenedioxy-2-nitrophenyl)-2-ethoxycarbonyl-1,2-ethanediyl acetal (Compound IVb) was prepared in a yield of 21% using Compound IIIb in place of Compound IIIa in the method for preparing Compound IVa. Compound IVb was obtained as an oil after purification by chromatography on silica gel.

$^1$H NMR delta 1.30 (t, J=7 Hz, 3H, —OCH$_2$CH$_3$), 1.35 (t, J=5 Hz, 1H, bridgehead H), 1.68 (t, J=5 Hz, 1H, bridgehead H), 1.82–1.93 (m, 4H, quadricyclane H's), 4.30 (m, 2H, —OCH2CH3), 4.44 (d, J=6 Hz, 1H, EtO$_2$C—CH—OR), 6.07 (d, J=5 Hz, 1H, Ar—CH—OR), 6.15 (d, J=4, 1H, —O—CHH'—O—), 6.16 (d J=4 Hz, 1H, —O—CH H'—O—), 7.44 (s, 1H, Ar H3), 7.59 (s, 1H, Ar H6).

Compound IVb was isomerized to bicyclo[2.2.1]hepta-2,5-diene-7-one, cyclic 1-(4,5-methylenedioxy-2-nitrophenyl)-2-ethoxycarbonyl-1,2-ethanediyl acetal (NP-CO/Et) (Compound Vb) with the palladium catalyst described above to give a yield of 53% of Compound Vb after chromatography using 25% (v/v) ethyl acetate in hexane. This compound was a light brown oil.

$^1$H NMR delta 1.31 (t, J=7 Hz, 3H, —OCH$_2$CH$_3$), 3.71 (m, 1H, bridgehead H), 3.95 (m, 1H, bridgehead H), 4.24 (d J=5 Hz, 1H, EtO$_2$C—CH—OR), 4.28 (m, 2H, —OCH$_2$CH$_3$), 5.84 (d, J=5 Hz, 1H, Ar—CH—OR), 6.14 (s, 1H, —O—CHH'—O—), 6.15 (s, 1H, —O—CHH'—O—), 6.76–6.83 (m, 4H, vinyl H's), 7.12 (s, 1H, Ar H-3), 7.54 (s, 1H, Ar H-6).

Bicyclo[2.2.1]hepta-2,5-diene-7-one, cyclic 1-(4,5-methylenedioxy-2-nitrophenyl)-2-carboxy-1,2-ethanediyl acetal, sodium salt (NP-CO/Na) (Compound VIb) was obtained, in quantitative yield, by saponification of Compound Vb in the same manner as described above for obtaining Compound VIa.

$^1$H NMR delta 3.80 (b, 2H, bridgehead H), 4.22 (d, J=5 Hz, 1H, —O$_2$C—CH—O—), 5.75 (d, J=5 Hz, 1H, Ar—CH—O—), 6.20 (s, 2H, —O—CH$_2$—O—), 6.75–6.90 (m, 4H, vinyl H), 7.18 (s, 1H, Ar H-3), 7.60 (s, 1H, Ar H-6).

Bicyclo[2.2.1]hepta-2,5-diene-7-one, cyclic 1-(4,5-methylenedioxy-2-nitrophenyl)-2-acetoxymethyloxycarbonyl-1,2-ethanediyl acetal (NP-CO/AM) (Compound VIIb) was prepared using the same procedure for the preparation of Compound VIIa except that Compound VIb was substituted for Compound VIa. Compound VIIb was obtained in 60% yield after chromatography using 2.5% (v/v) ethyl acetate in benzene, as an amber oil.

$^1$H NMR delta 2.16 (s, 3H, —O(CO)—CH$_3$), 3.70 (b, 1H, bridgehead H), 3.98 (b, 1H, bridgehead H), 4.27 (d J=6 Hz, 1H, RO$_2$C—CH—O—), 5.97–5.84 (m, 3H, —CO$_2$C H$_2$—OAc, Ar—CH—OR), 6.15 (s, 2H, —O—C H$_2$—O—), 6.73–6.82 (m, 4H, vinyl H), 7.13 (s, 1H, Ar H-3), 7.58 (s, 1H, Ar H-6).

SYNTHESIS EXAMPLE 3

Ethyl 3-(4,5-dimethoxy-2-nitrophenyl)propenoate (Compound Ic) was synthesized using the same procedure for preparing Compound Ib, but using 5-nitroveratral instead of 5-nitropiperonal. The resulting yellow solid (M.p. 149.7°–150.6° C.) was obtained in 76% yield after recrystallization from absolute ethanol.

$^1$NMR delta 1.35 (t, J=7 Hz, 3H, —O—CH$_2$—CH$_3$), 3.98 (s, 3H, p-Ar—OCH$_3$), 4.00 (s, 3H, m-Ar—O—CH$_3$), 4.29 (q, J=7, 2H, o-CH$_2$—CH$_3$), 6.30 (d, J=16 Hz, 1H, —CH═C HCO$_2$Et), 6.97 (S, 1H, veratryl H-2), 7.64 (s, 1H, veratryl H-5), 8.21 (d, J=16 Hz, Ar—CH═CH—).

The same dihydroxylation procedure used above for synthesizing Compound IIa was utilized for making ethyl 2,3-dihydroxy-3-(4,5-dimethoxy-2-nitrophenyl)propionate (Compound IIc) using Compound Ic in place of Compound Ia. Compound IIc was recrystallized from an ethanol/water mixture. The synthetic yield, and physical properties were as follows:

Powdery, yellow needles obtained in 86% yield after recrystallization. M.p. 167.5°–168.3° C.

$^1$NMR delta 1.26 (t, J=7 Hz, 3H, —O—CH$_2$—CH$_3$), 3.92 (s, 3H, —OCH$_3$), 3.94 (s, 3H, —OCH$_3$), 4.10 (d, J=8 Hz, 1H, —CH—OH—CO$_2$Et), 4.20 (q, J=7 Hz, 2H, —OC H$_2$—CH$_3$), 4.43 (d, J=8 Hz, 1H, —CH—OH—CO$_2$Et), 4.96 (d, J=6 Hz, 1H, Ar—CH—OH—), 5.79 (d, J=6 Hz, 1H, Ar—CH—OH—), 7.54 (s, 1H, veratryl 5-H), 7.60 (s, 1H, veratryl 2-H).

Ethyl 2,3-bis(trimethylsilyloxy)-3-(4,5-dimethoxy-2-nitrophenyl)propionate (Compound IIIc) was synthesized from Compound IIc using the above procedure for preparing Compound IIIa from Compound IIa. Compound IIIc did not require purification. The physical and spectral data were as follows:

Off-white powdery solid obtained in 85% yield. M.p. 151.1°–153° C.

$^1$NMR delta −0.17 (s, 9H, EtO$_2$C—CH—OSi(CH$_3$)$_3$), −0.00 (s, 9H, Ar—CH—OSi(CH$_3$)$_3$), 1.36 (t, J=7 Hz, 3H, —OCH$_2$CH$_3$), 3.96 (s, 3H, —OCH$_3$), 3.98 (s, 3H, —OC H$_3$), 4.28 (q, J=7, —OCH$_2$CH$_3$), 4.66 (d, J=2 Hz, 1H, EtO$_2$C—CH—OTMS), 5.95 (d, J=2 Hz, 1H, Ar—C H—OTMS), 7.43 (s, 1H, Ar 4H), 7.59 (s, 1H, Ar 6-H).

Tetracyclo[3.2.0.0$^{2,7}$.0$^{4,6}$]heptan-3-one, cyclic 1-(4,5-dimethoxy-2-nitrophenyl)-2-ethoxycarbonyl-1,2-ethanediyl acetal (Compound IVc) was prepared in a yield of 38% using Compound IIIc in place of Compound IIIa in the method for preparing Compound IVa. Compound IVc was obtained as an oil after purification by chromatography on silica gel.

1H NMR delta 1.31 (t, J=7 Hz, 4H, —OCH$_2$—CH$_3$ and bridgehead H), 1.72 (dt, J=5, 1 Hz, 1H, bridgehead H), 1.86–1.93 (m, 4H, quadicyclane H's), 3.97 (s, 3H, —OC H$_3$), 3.99 (s, 3H, —OCH$_3$), 4.30 (m, 2H, —OCH$_2$CH$_3$) 4.46 (d J=5 Hz, 1H, EtO$_2$C—CH—OR), 6.19 (d J=6 Hz, 1H, Ar—CH—OR), 7.49 (s, 1H, Ar H3), 7.9 (s, 1H, Ar H6).

Compound IVc was isomerized to bicyclo[2.2.1]hepta-2,5-diene-7-one, cyclic 1-(4,5-dimethoxy-2-nitrophenyl)-2-ethoxycarbonyl-1,2-ethanediyl acetal (NV-CO/Et) (Compound Vc) with the palladium catalyst described above to give a yield of 86% of Compound Vc after chromatography using 25% (v/v) ethyl acetate in hexane. This compound was a light brown oil.

$^1$NMR delta 1.32 (t, J=7 Hz, 3H, —OCH$_2$CH$_3$), 3.70 (b, 1H, bridgehead H), 3.9t (s, 3H, —OCH$_3$), 3.98 (v, 1H, bridgehead H), 4.03 (s, 3H, —OCH$_3$), 4,27 (d J=4 Hz, 1H, EtO$_2$C—CH—OR), 4.25–4.33 (m, 2H, —OCH$_2$CH$_3$), 5.95 (d, J=4 Hz, 1H, Ar—CH—OR), 6.74–6.82 (m, 4H, vinyl H's), 7.46 (s, 1H, Ar H-3), 7.65 (s, 1H, Ar H-6).

Bicyclo[2.2.1 ]hepta-2,5-diene-7-one, cyclic 1-(4,5-dimethoxy 2-nitrophenyl)-2-carboxy-1,2-ethanediyl acetal, sodium salt (NV-CO/Na) (Compound VIc) was obtained, in quantitative yield, by saponification of Compound Vc in the same manner as described above for obtaining Compound VIa.

$^1$NMR delta 3.83 (b, 2H, bridgehead H), 3.89 (s, 3H, —OCH$_3$), 4.00 (s, 3H, —OCH$_3$), 4.26 (d, J=5 Hz, 1H, —O$_2$C—CH—O—), 5.82 (d, J=5 Hz, 1H, Ar—CH—O—), 6.85–6.95 (m, 4H, vinyl H), 7.15 (s, 1H, Ar H-3), 7.75 (s, 1H, Ar 6-H).

Bicyclo[2.2.1]hepta-2,5-diene-7-one, cyclic 1-(4,5-dimethoxy-2-nitrophenyl)-2-acetoxymethyloxycarbonyl-1,2-ethanediyl acetal (NV-CO/AM) (Compound VIIc) was prepared using the same procedure for the preparation of Compound VIIa except that Compound VIc was substituted for Compound VIa. Compound VIIc was obtained in 73% yield after chromatography using 2.5% (v/v) ethyl acetate in benzene, as an amber oil.

$^1$NMR delta 2.16 (s, 3H, —O(CO)—CH$_3$), 3.70 (b, 1H, bridgehead H), 3.95 (s, 3H, —OCH$_3$), 4.00 (b, 1H, bridgehead H), 4.03 (s, 3H, —OCH$_3$), 4.30 (d J=5 Hz, 1H, RO$_2$C—CH—O—), 5.83 (ab quartet, J=10 Hz, 2H, —CO$_2$CH$_2$—OAc), 5.91 (d, J=5 Hz, 1H, Ar—CH—OR), 6.78–6.81 (m, 4H, vinyl H), 7.15 (s, 1H, Ar H-3), 7.64 (s,1H, Ar H-6).

EXAMPLE 1

In vitro Release of CO

In this example, the following caged CO, NF-CO/Na was employed:

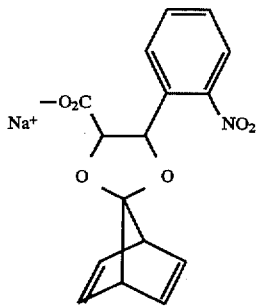

More specifically, a 100 μM aqueous solution of NF-CO/Na in water (pH 7.0) was exposed for 8 min to UV light from a 50 watt mercury lamp (filtered through 2.0 mm thick UG1 glass). The resulting UV spectra, as well as that of the solution prior to photolysis with UV light, are shown in FIG. 1.

As shown in FIG. 1, exposure of the aqueous sample converted the starting caged compound to a product with a distinctly different spectrum.

It can be seen from the spectra in FIG. 1 that the caged compound itself negligibly absorbs light beyond 400 nm. Thus, in order to show that UV photolysis actually generated CO, reduced hemoglobin was used as an indicator; reduced hemoglobin is a well-known indicator for CO: showing distinct spectroscopic changes in the 400 to 700 nm range upon binding to CO.

Figure 2:
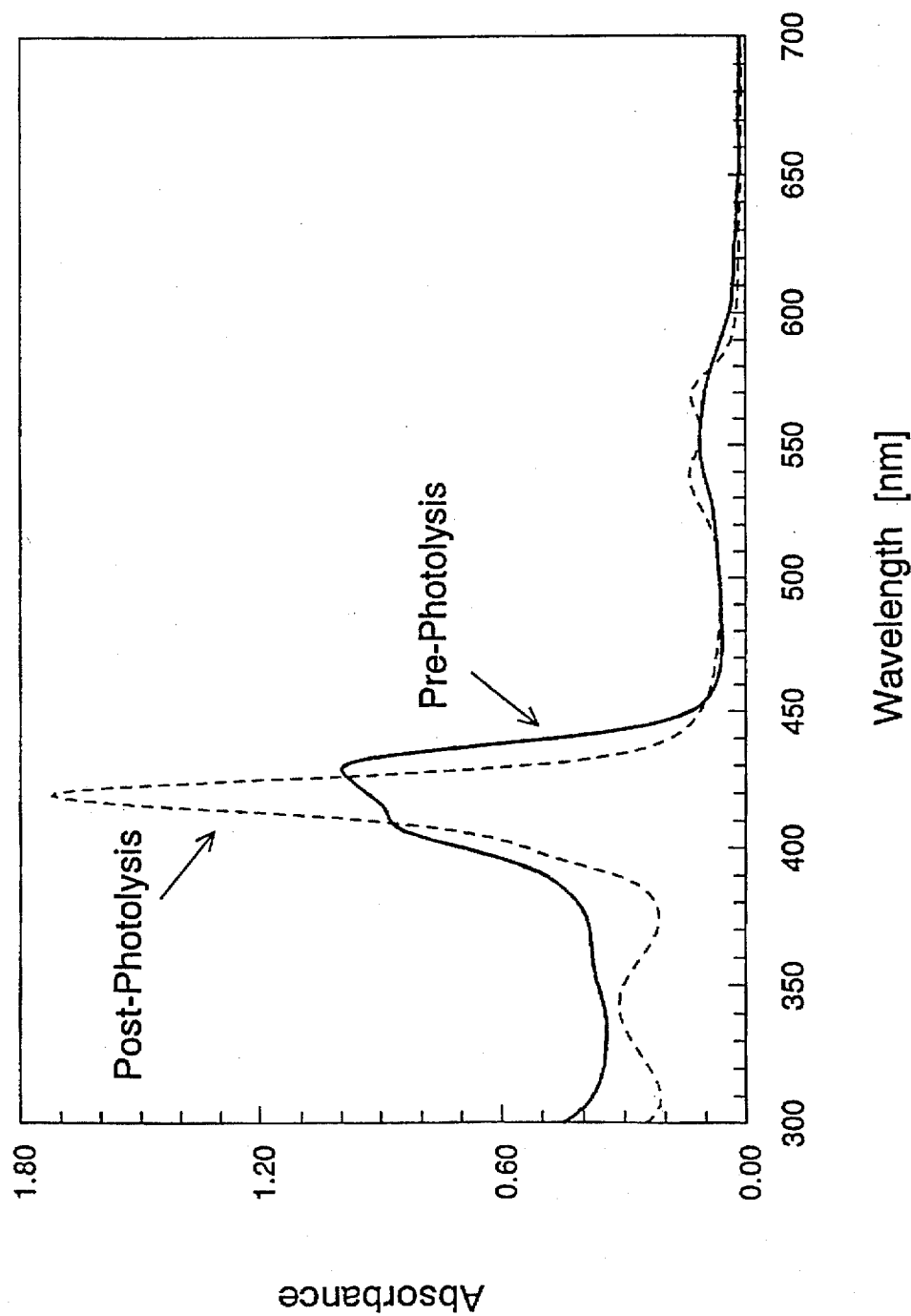
FIG. 2 shows the visible spectra of an aqueous solution of NF-CO/Na containing hemoglobin before and after photolysis with UV light.

More specifically, an aqueous solution containing 3.0 μM nitrogen-purged ovine ferrous hemoglobin and 150 μM NF-CO/Na in 20 mM phosphate buffer (pH 8.0) was exposed for 4 min to UV light from a 50 watt mercury lamp (filtered through 2.0 mm thick UG1 glass). The resulting visible spectra, as well as that of the solution prior to photolysis with UV light, are shown in FIG. 2. Further, the 450–650 nm region from FIG. 2 is shown in FIG. 3 on an expanded scale to reveal the characteristic shape changes in the long-wavelength absorption band of the hemoglobin upon binding CO.

Figure 3:
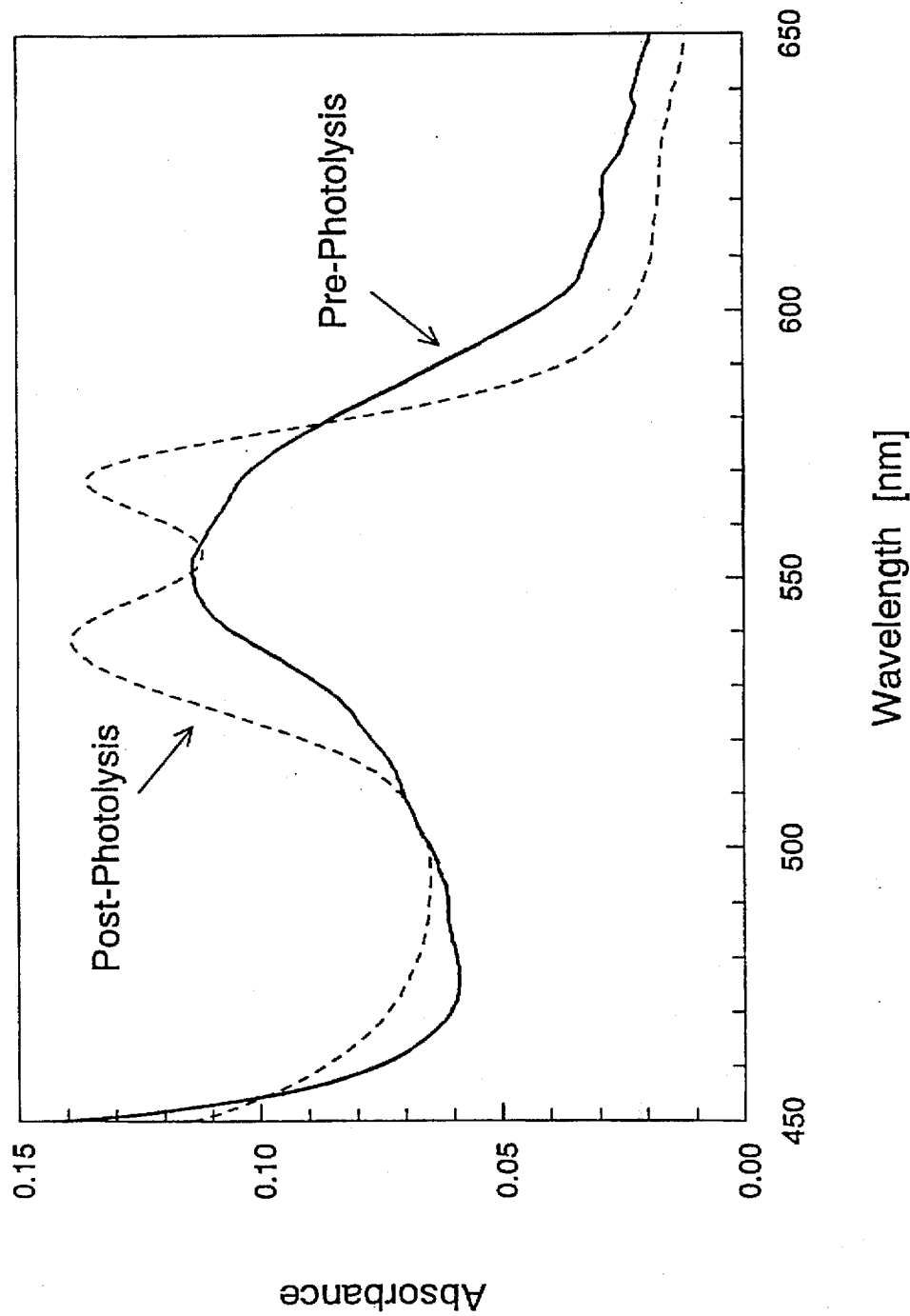
FIG. 3 shows the 450–650 nm region from FIG. 2 on an expanded scale.

As shown in FIGS. 2 and 3, photolysis of the caged compound releases CO, which bound to the hemoglobin, and thus altered its visible spectrum.

To ascertain that the changes in the hemoglobin spectrum are due to binding of photo-generated CO, and not due to other side-products of the photochemical reaction, the hemoglobin experiment was repeated using the NF caging group alone, as photolysis of NF is expected to generate the same side-products as the authentic caged CO.

No change in the hemoglobin absorption spectrum was observed when NF was photolyzed in the presence of hemoglobin. These results indicate that the spectral changes shown in FIGS. 2 and 3 are indeed the result of binding of photo-generated CO by hemoglobin.

EXAMPLE 2

Stimulation of Cyclic GMP Production by In Vivo Release of CO

The efficacy of use of the caged CO compounds of the present invention in living cells was tested in primary smooth muscle cells isolated from the aortas of Sprague-Dawley rats.

More specifically, primary smooth muscle cells from the aortas of Sprague-Dawley rats were seeded into replicate 3.5-cm cell culture dishes, and allowed to grow to confluence in Dulbecco's modified Eagle medium (DMEM) at 37° C. in a 5% CO$_2$/air incubator. At the start of the experiment, DMEM was removed from all of the dishes, and each dish was treated at 37° C. for 5 min with 2.0 ml of 200 μM 3-isobutyl-1-methylxanthine (IBMX) in Dulbecco's phosphate-buffered saline (DPBS) to inhibit phosphodiesterases that would destroy cyclic GMP (cGMP). At the end of 5 min, the following treatments were administered:

(1) 3 dishes were treated for 8 min with about 600 μM CO gas in DPBS;

(2) 3 dishes, which had been pre-loaded for 1 hr with 50 μM NV-CO/AM in DMEM to allow accumulation of NV-CO/AM reagent within the smooth muscle cells, were each illuminated with UV light from a 50 watt mercury lamp (filtered through 2.0 mm thick UG1 glass) for two, 5 sec intervals, at 0 and 4 minutes during an 8 min incubation in DPBS;

(3) 3 control dishes were simply incubated in DPBS.

Throughout the 8 min treatments, 200 μM IBMX was present in all of the dishes. Next, DPBS was removed by suction from all of the dishes, which were then rapidly frozen in liquid nitrogen, and thawed (3 cycles) to lyse the cells and release the cellular contents. Each dish was triturated repeatedly with small volumes of 70% (v/v) ice-cold ethanol to extract the soluble cellular contents. Ethanol fractions from each dish were combined and sedimented in a microcentrifuge, and the supernatant collected. Each sediment pellet was washed once with 100 μl of 70% (v/v) ethanol, and the washing was combined with the original supernatant. All of the ethanol samples were then dried in a centrifugal evaporator.

The cGMP content of each dried sample was analyzed with an enzyme immunoassay kit (Amersham Life Science). Quantitative comparisons of the results are shown as a bar graph in FIG. 4.

Figure 4:
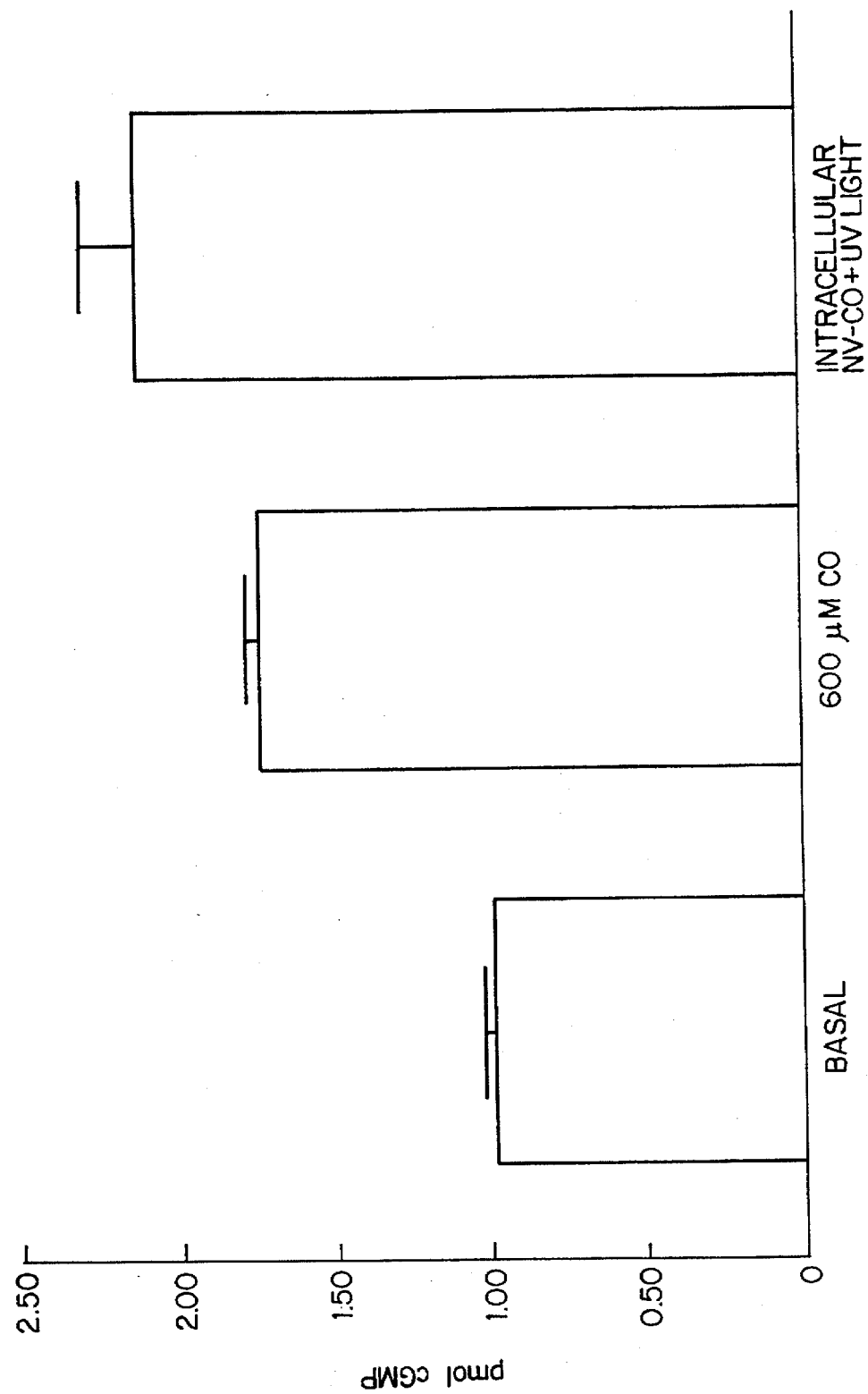
FIG. 4 shows the effect of CO photorelease on cGMP content in rat aortic smooth muscle cells using NV-CO/AM.

As shown in FIG. 4, confluent cultures exhibited marked increase in intracellular cGMP levels (1) when treated with CO gas, and (2) when exposed to 5 sec flashes of UV light after having accumulated NV-CO intracellularly via incubation with the AM ester.

These results show that the compounds of the present invention can be loaded into living cells through use of the AM ester, and that the effects of CO photorelease therefrom are indistinguishable from those caused by direct exposure to CO gas.

While the invention has been described in detail, and with reference to specific embodiments thereof, it will be apparent to one of ordinary skill in the art that various changes and modifications can be made therein without departing from the spirit and scope thereof.

What is claimed:

1. A compound represented by Formula (I):

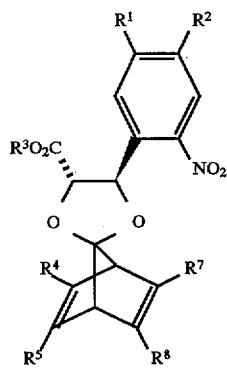

wherein $R^1$ and $R^2$, which may be the same or different, are each selected from the group consisting of hydrogen, hydroxy, alkanoyloxymethoxy, wherein the alkanoyloxy moiety has from 1 to 5 carbon atoms, alkyl having from 1 to 5 carbon atoms, and alkoxy having from 1 to 5 carbon atoms; with the proviso that $R^1$ and $R^2$ may be combined to form a methylenedioxy (O—$(CH_2)_n$—O) linkage, wherein n represents an integer of from 1 to 4;

wherein $R^3$ is selected from the group consisting of hydrogen; alkyl having from 1 to 5 carbon atoms; alkanoyloxymethyl, wherein the alkanoyloxy moiety has from 1 to 5 carbon atoms; alkali metal ion; alkaline earth metal ion; and $NR_4$, wherein each R, which may be the same or different, is selected from the group consisting of hydrogen, alkyl having from 1 to 5 carbon atoms, phenyl, tolyl and benzyl; and wherein $R^4$, $R^5$, $R^6$, $R^7$, which may be the same or different, are each selected from the group consisting of hydrogen, cyano, $CONHR^1$, $CONR^1_2$, $SO_2NHR^1$, $SO_2NR^1_2$, $CH_2R^1$, $CH_2CONHR^1$, $CH_2CONR^1_2$, $CO_2R^3$ and $SO_3R^3$, wherein $R^1$ and $R^3$ are as defined above.

2. The compound of claim 1, wherein $R^1$ and $R^2$ are each selected from the group consisting of alkanoyloxymethoxy, wherein the alkanoyloxy moiety has from 2 to 3 carbon atoms, alkyl having from 1 to 2 carbon atoms, and alkoxy having from 1 to 2 carbon atoms, or when $R^1$ and $R^2$ are combined, n represents an integer of from 1 to 2;

wherein $R^3$ is selected from the group consisting of alkyl having from 1 to 2 carbon atoms; alkanoyloxymethoxy, wherein the alkanoyloxy moiety has from 2 to 3 carbon atoms; alkali metal ion selected from the group consisting of lithium, sodium, potassium and cesium; calcium and magnesium; and $NR_4$, wherein each R is hydrogen.

3. The compound of claim 1, wherein $R^1$ and $R^2$ are each selected from the group consisting of hydrogen and methoxy, or when $R^1$ and $R^2$ are combined, they form —$OCH_2O$—;

$R^3$ is selected from the group consisting of methyl, ethyl, acetoxymethyl, sodium and potassium; and $R^4$, $R^5$, $R^6$, $R^7$ are each hydrogen.

4. The compound of claim 1, wherein said compound is selected from the group consisting of bicyclo[2.2.1]hepta-2,5-diene-7-one, cyclic 1-(2-nitrophenyl)-2-methoxycarbonyl-1,2-ethanediyl acetal; bicyclo[2.2.1]hepta-2,5-diene-7-one, cyclic 1-(2-nitrophenyl)-2-carboxy-1,2-ethanediyl acetal, sodium salt; bicyclo[2.2.1]hepta-2,5-diene-7-one, cyclic 1-(2-nitrophenyl)-2-acetoxymethyloxycarbonyl-1,2-ethanediyl acetal; bicyclo[2.2.1]hepta-2,5-diene-7-one, cyclic 1-(4,5-dimethoxy-2-nitrophenyl)-2-ethoxycarbonyl-1,2-ethanediyl acetal; bicyclo [2.2.1]hepta-2,5-diene-7-one, cyclic 1-(4,5-dimethoxy 2-nitrophenyl)-2-carboxy-1,2-ethanediylacetal, sodium salt; bicyclo[2.2.1]hepta-2,5-diene-7-one, cyclic 1-(4,5-dimethoxy-2-nitrophenyl)-2-acetoxymethyloxycarbonyl-1,2-ethanediyl acetal; bicyclo [2.2.1]hepta-2,5-diene-7-one, cyclic 1-(4,5-methylenedioxy-2-nitrophenyl)-2-ethoxycarbonyl-1,2-ethanediyl acetal; bicyclo[2.2.1]hepta-2,5-diene-7-one, cyclic 1-(4,5-methylenedioxy-2-nitrophenyl)-2-carboxy-1,2-ethanediyl acetal, sodium salt; and bicyclo[2.2.1]hepta-2,5-diene-7-one, cyclic 1-(4,5-methylenedioxy-2-nitrophenyl)-2-acetoxymethyloxycarbonyl-1,2-ethanediyl acetal.

5. The compound of claim 1, wherein said compound is present in an aqueous solution at a concentration of about $10^{-5}$ to $10^{-1}$M.

6. The compound of claim 5, wherein said aqueous solution has a pH of about 6 to 8.

7. A method for producing carbon monoxide comprising the step of UV irradiating a compound represented by Formula (I):

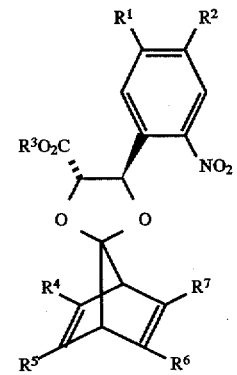

wherein $R^1$ and $R^2$, which may be the same or different, are each selected from the group consisting of hydrogen, hydroxy, alkanoyloxymethoxy, wherein the alkanoyloxy moiety has from 1 to 5 carbon atoms, alkyl having from 1 to 5 carbon atoms, and alkoxy having from 1 to 5 carbon atoms; with the proviso that $R^1$ and $R^2$ may be combined to form a methylenedioxy (O—$(CH_2)_n$—O) linkage, wherein n represents an integer of from 1 to 4;

wherein $R^3$ is selected from the group consisting of hydrogen; alkyl having from 1 to 5 carbon atoms; alkanoyloxymethyl, wherein the alkanoyloxy moiety has from 1 to 5 carbon atoms; alkali metal ion; alkaline earth metal ion; and $NR_4$, wherein each R, which may be the same or different, is selected from the group consisting of hydrogen, alkyl having from 1 to 5 carbon atoms, phenyl, tolyl and benzyl; and wherein $R^4$, $R^5$, $R^6$, $R^7$, which may be the same or different, are each selected from the group consisting of hydrogen, cyano, $CONHR^1$, $CONR^1_2$, $SO_2NHR^1$, $SO_2NR^1_2$, $CH_2R^1$, $CH_2CONHR^1$, $CH_2CONR^1_2$, $CO_2R^3$ and $SO_3R^3$, wherein $R^1$ and $R^3$ are as defined above.

8. The method of claim 7, wherein $R^1$ and $R^2$ are each selected from the group consisting of alkanoyloxymethoxy, wherein the alkanoyloxy moiety has from 2 to 3 carbon atoms, alkyl having from 1 to 2 carbon atoms, and alkoxy having from 1 to 2 carbon atoms, or when $R^1$ and $R^2$ are combined, n represents an integer of from 1 to 2;

wherein $R^3$ is selected from the group consisting of alkyl having from 1 to 2 carbon atoms; alkanoyloxymethoxy, wherein the alkanoyloxy moiety has from 2 to 3 carbon atoms; alkali metal ion selected from the group consisting of lithium, sodium, potassium and cesium; calcium; and $NR_4$, wherein each R is hydrogen.

9. The method of claim 7, wherein $R^1$ and $R^2$ are each selected from the group consisting of hydrogen and methoxy, or when $R^1$ and $R^2$ are combined, they form —$OCH_2O$—;

$R^3$ is selected from the group consisting of methyl, ethyl, acetoxymethyl, sodium and potassium; and $R^4$, $R^5$, $R^6$, $R^7$ are each hydrogen.

10. The method of claim 7, wherein said compound is selected from the group consisting of bicyclo[2.2.1]hepta-2,5-diene-7-one, cyclic 1-(2-nitrophenyl)-2-methoxycarbonyl-1,2-ethanediyl acetal; bicyclo[2.2.1]hepta-2,5-diene-7-one, cyclic 1-(2-nitrophenyl)-2-carboxy-1,2-ethanediyl acetal, sodium salt; bicyclo[2.2.1]hepta-2,5-diene-7-one, cyclic 1-(2-nitrophenyl)-2-acetoxymethyloxycarbonyl-1,2-ethanediyl acetal; bicyclo [2.2.1]hepta-2,5-diene-7-one, cyclic 1-(4,5-dimethoxy-2-nitrophenyl)-2-ethoxycarbonyl-1,2-ethanediyl acetal; bicyclo [2.2.1]hepta-2,5-diene-7-one, cyclic 1-(4,5-dimethoxy 2-nitrophenyl)-2-carboxy-1,2-ethanediylacetal, sodium salt; bicyclo[2.2.1]hepta-2,5-diene-7-one, cyclic 1-(4,5-dimethoxy-2-nitrophenyl)-2-acetoxymethyloxycarbonyl-1,2-ethanediyl acetal; bicyclo [2.2.1]hepta-2,5-diene-7-one, cyclic 1-(4,5-methylenedioxy-2-nitrophenyl)-2-ethoxycarbonyl-1,2-ethanediyl acetal; bicyclo[2.2.1]hepta-2,5-diene-7-one, cyclic 1-(4,5-methylenedioxy-2-nitrophenyl)-2-carboxy-1,2-ethanediyl acetal, sodium salt; and bicyclo[2.2.1]hepta-2,5-diene-7-one, cyclic 1-(4,5-methylenedioxy-2-nitrophenyl)-2-acetoxymethyloxycarbonyl-1,2-ethanediyl acetal.

11. The method of claim 7, wherein said irradiating is carried out at a wavelength of about 300 to 400 nm.

12. The method of claim 7, wherein said irradiating is carried out at about 10° to 40° C.

13. The method of claim 7, wherein said compound is present in an aqueous solution at a concentration of about $10^{-5}$ to $10^{-1}$M.

14. The method of claim 12, wherein said aqueous solution has a pH of about 6 to 8.

15. The method of claim 7, wherein said irradiating is carried out after perfusing tissue or cultured cells with an aqueous solution containing said compound.

16. The method of claim 7, wherein said irradiating is carried out after microinjecting a cell with an aqueous solution containing said compound.

* * * * *